(12) United States Patent
Tsoukalis

(10) Patent No.: US 12,362,053 B2
(45) Date of Patent: Jul. 15, 2025

(54) DRUG LABELING AND SAFE DELIVERY

(71) Applicant: Micrel Medical Devices S.A., Koropi (GR)

(72) Inventor: Achilleas Tsoukalis, Anavyssos Attica (GR)

(73) Assignee: Micrel Medical Devices S.A., Koropi (GR)

( * ) Notice: Subject to any disclaimer, the term of this patent is extended or adjusted under 35 U.S.C. 154(b) by 1223 days.

(21) Appl. No.: 16/953,043

(22) Filed: Nov. 19, 2020

(65) Prior Publication Data

US 2021/0151162 A1    May 20, 2021

(30) Foreign Application Priority Data

Nov. 19, 2019  (EP) ..................................... 19210179
Dec. 19, 2019  (EP) ..................................... 19218037

(51) Int. Cl.
*A61M 5/142*    (2006.01)
*A61M 5/168*    (2006.01)
*G16H 20/17*    (2018.01)

(52) U.S. Cl.
CPC ............ *G16H 20/17* (2018.01); *A61M 5/142* (2013.01); *A61M 5/16831* (2013.01);
(Continued)

(58) Field of Classification Search
CPC ... G16H 20/17; A61J 2205/00; A61J 2205/10; A61J 2205/30; A61J 1/18;
(Continued)

(56) References Cited

U.S. PATENT DOCUMENTS 5,006,050 A * 4/1991 Cooke ..................... F04B 43/04
                                                        417/478
5,078,683 A * 1/1992 Sancoff .................. G16H 20/17
                                                        417/474
(Continued)

FOREIGN PATENT DOCUMENTS

EP    2 987 517 A1    2/2016
EP    3 231 467 A1    10/2017
EP    3 421 064 A1    1/2019

OTHER PUBLICATIONS

Extended European search report issued in European Patent Application No. 20208704.5, dated Apr. 15, 2021.

*Primary Examiner* — Adam Marcetich
*Assistant Examiner* — Ted Yang
(74) *Attorney, Agent, or Firm* — Bookoff McAndrews, PLLC

(57) ABSTRACT

An infusion device comprising a medication reservoir having at least a first port adapted to be coupled to an inlet port of an infusion equipment, and a first tag support adapted to support a first tag storing information about the content of the medication reservoir and to be read by a tag reader. The infusion device is characterized by a second tag support adapted to support a second tag storing information about the content of a separate vessel, in particular a vial, which content is to be discharged into said medication reservoir so as to mix it with the content of said medication reservoir, wherein said second tag support is provided to arrange and orientate the second tag to the tag reader and therefore to enable the tag reader to also read said second tag.

34 Claims, 7 Drawing Sheets

(52) U.S. Cl.
CPC ... *A61M 2205/11* (2013.01); *A61M 2205/502* (2013.01); *A61M 2205/60* (2013.01); *A61M 2205/6063* (2013.01); *A61M 2205/6072* (2013.01); *A61M 2205/6081* (2013.01)

(58) Field of Classification Search
CPC ...... A61M 2205/60; A61M 2205/6072; A61M 5/142; A61M 5/1407
See application file for complete search history.

(56) References Cited

U.S. PATENT DOCUMENTS

| | | | | |
|---|---|---|---|---|
| 5,873,731 | A * | 2/1999 | Prendergast | G09B 23/28 434/262 |
| 7,976,508 | B2 * | 7/2011 | Hoag | G16H 20/17 340/572.1 |
| 9,242,042 | B2 * | 1/2016 | Martin | A61M 5/1723 |
| 9,883,987 | B2 * | 2/2018 | Lopez | A61J 1/2096 |
| 10,629,298 | B2 | 4/2020 | Seufert | G16H 20/10 |
| 2001/0049608 | A1 * | 12/2001 | Hochman | G16H 20/17 700/214 |
| 2002/0038392 | A1 * | 3/2002 | De La Huerga | G16H 20/17 710/8 |
| 2003/0074223 | A1 * | 4/2003 | Hickle | A61J 1/14 705/2 |
| 2007/0018833 | A1 * | 1/2007 | Higashionji | B41J 13/103 340/572.7 |
| 2007/0135765 | A1 * | 6/2007 | Miller | A61M 5/16827 604/131 |
| 2008/0033368 | A1 * | 2/2008 | Fago | G16H 20/13 604/189 |
| 2008/0131362 | A1 * | 6/2008 | Rousso | A61M 5/1782 424/1.11 |
| 2009/0126825 | A1 * | 5/2009 | Eliuk | B65B 3/003 141/330 |
| 2010/0245056 | A1 * | 9/2010 | Braun | A61J 1/1425 340/10.42 |
| 2010/0300438 | A1 * | 12/2010 | Martin | G16H 20/17 128/203.14 |
| 2011/0021978 | A1 * | 1/2011 | Martin | A61M 5/16827 235/375 |
| 2011/0062703 | A1 * | 3/2011 | Lopez | A61M 39/22 285/129.1 |
| 2012/0037266 | A1 * | 2/2012 | Bochenko | A61J 1/2096 604/404 |
| 2012/0095415 | A1 * | 4/2012 | Sharvit | A61M 39/1011 604/244 |
| 2013/0018356 | A1 * | 1/2013 | Prince | G06Q 10/0833 604/506 |
| 2015/0001285 | A1 * | 1/2015 | Halbert | G16H 20/17 235/375 |
| 2016/0051750 | A1 * | 2/2016 | Tsoukalis | A61M 5/16813 235/375 |
| 2017/0255760 | A1 * | 9/2017 | Lee | G16H 20/10 |
| 2017/0290974 | A1 * | 10/2017 | Tsoukalis | A61M 5/1407 |
| 2018/0114598 | A1 * | 4/2018 | Kolberg | G16H 10/60 |
| 2018/0344572 | A1 * | 12/2018 | Zollinger | A61J 1/1406 |
| 2019/0001057 | A1 * | 1/2019 | Tsoukalis | G06K 7/10366 |
| 2019/0161229 | A1 * | 5/2019 | Mase | A61J 1/14 |
| 2020/0022873 | A1 * | 1/2020 | Naygauz | A61J 1/2037 |
| 2020/0107992 | A1 * | 4/2020 | Schmidlin | G06K 19/07773 |
| 2021/0154391 | A1 * | 5/2021 | Tennican | G06Q 10/08 |

\* cited by examiner

DRUG LABELING AND SAFE DELIVERY

RELATED APPLICATIONS

This application claims priority to EP Patent Application No. 19210179.8, filed on Nov. 19, 2019, and EP Patent Application No. 19218037.0, filed on Dec. 19, 2019, both of which are incorporated herein by reference in their entireties.

FIELD OF THE INVENTION

The present invention relates to an infusion device comprising a medication reservoir having at least a first port adapted to be coupled to an inlet port of an infusion equipment.

BACKGROUND OF THE INVENTION

Intravenous administration is the most common parenteral administration route, providing an immediate therapeutic effect by delivering a drug directly into the blood circulation. Small-volume parenteral applications (SVP) with a volume of less than 100 ml and large-volume parenterals (LVP) with a volume of 100 ml or greater are both used for the intermittent or continuous infusion of fluids or drugs.

Injectable dosage forms are the preferred formulation of large molecule drug products which are traditionally delivered via the intravenous (IV) admixture. A drug delivered intravenously is pumped directly into a patient's blood circulatory system and takes effect immediately. An admixture is used as a dried or lyophilized drug product, packaged in a vessel like a glass vial or ampoule. In order to enable a patient to imbibe the admixture, the dry powder concentrate must be diluted.

Premixed bags, however, can be injected into a patient without any mixing; they are packaged in plastic bags and ready-to-use. These premixed IV (intravenous) solutions eliminate the need for human intervention for preparing the drug product and are therefore the safest option for administration.

Advantages of premixed IV solutions in order to ensure patient safety, the Institute for Safe Medication Practices (ISMP) recommends the use of commercially prepared premixed bags instead of manually compounded sterile products. Similarly, opting for premixed bags as opposed to admixtures ensures compliance with the Joint Commission on the Accreditation of Healthcare Organizations (JCAHO) standards and U.S. Pharmacopeia 797 guidelines. These guidelines state: [1] Medications should be available in a ready to administer form whenever possible; [2] drug concentrations should be standardized; [3] medications should be available to meet patient needs when the pharmacy is closed; and [4] preparation of admixtures by a nursing staff should be minimized. By eliminating the need for admixtures, premixed bags manufactured in a cGMP compliant facility provide the highest level of safety available. In addition to a reduction of the risk of medical error, the threat of microbial contamination is greatly decreased with a premixed bags. Admixtures prepared in pharmacies are particularly vulnerable to process contamination. This is due to an inconsistent staffing and a variable environment of the compound area—variables that are eliminated when using premixed bags.

During the solution-mixing process, the staff might easily select an incorrect amount of a drug or an incorrect type or amount of solvent, without realizing they've done so. The solution would then be mixed incorrectly, but the tag or label would indicate the intended dose and solution, making the error invisible to the person administering the drug. Human factors studies have shown that the risk of such errors is especially high when workers are busy, distracted, tired or working in an environment not designed for safety. The use of pre-mixed solutions reduces the possibility of an adverse drug application due to a mixing error. Pre-mixing also saves time for the pharmacy and nursing staff.

Except for the aforementioned admixture of a wrong solution drug, infusion related medication errors, in particular with regard to name and concentration, usually occur since when using LVP pumps the drug or medication reservoir is mounted at the top of a pole and the pump is attached at the middle of the pole, so that it is up to the discretion of the nurse to indicate to the pump to which of many medication reservoirs available on top of the pole it is connected. In EP 2 987 517 A1, EP 3 231 467 A1 and EP 3 421 064 A1 it has been shown how a pump can be close to the drug reservoir and read an ID tag anytime placed on it or on a plate over a connecting tube.

It is an object of the present invention to provide an infusion device which assures sufficient safety with the preparation of an admixture in a medication reservoir.

SUMMARY OF THE INVENTION

In order to achieve the above and further objects, according to a first aspect of the present invention there is provided an infusion device comprising a medication reservoir having at least a first port adapted to be coupled to an inlet port of an infusion equipment, and a first tag support adapted to support a first tag storing information about the content of the medication reservoir and to be read by a tag reader, characterized by a second tag support adapted to support a second tag storing information about the content of a separate vessel, in particular a vial, which content is to be discharged into said medication reservoir so as to mix it with the content of said medication reservoir, wherein said second tag support is provided to arrange and orientate the second tag to the tag reader and therefore to enable the tag reader to also read said second tag.

According to a second aspect of the present invention, there is provided a method for preparing an admixture, comprising the steps of providing a medication reservoir which includes a first content, in particular a first medical substance being preferably a dilutor, and is marked by a first tag storing information about the first content, providing a separate vessel, in particular a vial, which includes a second content, in particular a second medical substance, preferably being a diluent, and marked by a second tag storing information about the second content, transferring the second content from the vessel into the medication reservoir in order to mix the second content with the first content and, hence, to prepare an admixture within the medication reservoir, and providing a tag reader which reads both the first and second tags at the same time either before or after the emptying of the separate vessel.

By the present invention errors are prevented since all dilution parts are visible to a tag reader of the infusion system for both diluent and diluter.

In particular, the present invention deals with a drug device combination, where a reservoir with medication and an infusion system are combined as a system to avoid medication errors from both categories described above, i.e. a wrong dilution description and a wrong medication (from many ones available close to the pump) delivered. For doing so, it is provided a novel reservoir preferably having a flexible body as those used for LVP pumps, preferably with hanging means like a hole on top, and connecting connectors at the bottom, pharmaceutically prefilled by a solution or premix drug, or empty for compounding. Further, it is provided a holder for a separate vessel, in particular a diluent drug vial, close to the fluidic connection for the infusion set of the infusion system, and an electronically and/or optically readable tag near to it, so that preferably the infusion system can read a vessel label tag and a reservoir tag in one reading process. In particular, the infusion system, which then communicates with a medical health record of the patient and receives drug library from the care system, can evaluate whether or not the drug name and concentration and the infusion programming are according to prescription and allows infusion or alarms not allowing it automatically.

In particular, the present invention consists of four parts:
a) Infusion system scanning two tags of drug and diluter together any time before the infusion starts or during it, wherein for doing so the two tags are arranged close to each other so as to be read by preferably one reading;
b) evidence on diluter and drug tag data kept during the entire infusion without the need of manual inscription;
c) dilution concentration calculation by the infusion system so as to avoid manual errors;
d) the nursing staff can check anytime if correct drug and concentration is delivered to patient according to the prescription.

Such a drug-device combination solves a problem by adjusting both the drug production and infusion pump systems to collaborate together so to exclude medication errors of both types as described above.

In particular, the present invention uses a special reservoir for drug-device combination to be used with a specific pump that can read both the diluent and diluter tags and calculates the concentration, so that, if used together, medication errors may be prevented, like error prone hand writing adhesive label with constituents.

Preferred embodiments and modifications of the present invention are defined in the dependent claims.

According to a preferred embodiment, said first tag support and said second tag support are provided to arrange and orientate both the first and second tags so as to enable the tag reader to read not only said first tag but at the same time also said second tag, in particular essentially in the same perspective and/or in the same viewing window.

According to a further preferred embodiment, said second tag support is arranged adjacent and/or close to said first tag support and/or said first tag support and/or said second tag support is provided adjacent and/or close to said first port of said medication reservoir.

According to a further preferred embodiment, said first tag support forms a first tag support portion or region provided at said medication reservoir and said second tag support forms a second tag support portion or region also provided at said medication reservoir, wherein preferably said first tag support region or portion is provided to accommodate said first tag by attaching or printing it at said first tag support region or portion and/or preferably said second tag support region or portion is provided to accommodate said second tag by self adhesively attaching it to said second tag support region or portion.

According to a further preferred embodiment, said first tag support and/or said second tag support is provided adjacent and/or close to a lower edge portion of said medication reservoir and/or hangs down from a lower edge portion of said medication reservoir.

According to a further preferred embodiment, a protrusion is arranged at said medication reservoir, wherein according to a modification of this embodiment, said protrusion is provided with said first tag support, wherein preferably said protrusion comprises a first tag support portion which forms said first tag support, wherein said protrusion may be additionally provided with said second tag support, wherein preferably said protrusion comprises a second tag support portion which forms said second tag support.

According to a further preferred embodiment, there is provided a vessel holder which is adapted to removably attach or hold the vessel.

According to a modification of the aforementioned embodiment, said vessel holder is arranged at said protrusion, wherein said vessel holder may be arranged at said medication reservoir.

According to a further modification of the aforementioned embodiment, said vessel holder is provided to hold the vessel in an essentially vertical orientation with its opening facing upwards when the infusion device is in its operational mode.

According to a further modification of the aforementioned embodiment, said vessel holder is provided to hold the vessel in an essentially horizontal orientation with its opening facing sideways when the infusion device is in its operational mode, wherein preferably said vessel holder is further provided to hold the vessel with its second tag facing downwards.

According to a further modification of the aforementioned embodiment, said second tag support is comprised of said vessel holder which is adapted to removably attach such a vessel which comprises the second tag and is provided to hold the vessel so as to orientate its second tag to the tag reader, wherein said vessel holder may comprise a hollow body adapted to accommodate the vessel and including an opening which is provided to enable the second tag of the vessel to be exposed and to be read by the tag reader.

According to a further modification of the aforementioned embodiment, the vessel holder is provided as a pocket which preferably is at least partly transparent and/or preferably made of the same material as the medication reservoir.

According to an alternative modification of the aforementioned embodiment, said vessel holder comprises a clamping mechanism for holding the vessel by clamping effect, wherein said hollow body may have a tubular shape with an essentially "Ω"-like cross section, said opening may extend over an angular range less than 180 degrees, preferably about 150 degrees, in the cross section plane and further extends essentially along the entire length of the hollow body in an orientation transversely to said cross section plane, and said hollow body may comprise elastic material at least in its portions bounding said opening.

According to a further preferred embodiment, said medication reservoir comprises a second port adapted to be coupled to the opening of the vessel, wherein the second port may comprise a connector which may be a tap closing connector or an elastic self-closing connector, wherein said second port at said medication reservoir may be arranged adjacent to said vessel holder, but in such a distance thereto that there is enough space which allows attachment of the vessel to said vessel holder and detachment of the vessel from said vessel holder, and wherein said second port and vessel holder may be arranged relative to each other so that said second port essentially faces to the opening of the vessel when attached to said vessel holder.

Preferably, said medication reservoir, in particular its first port, is provided to support the tag reader.

According to a further preferred embodiment, the tag reader is part of the claimed device.

According to a modification of the aforementioned embodiment, said tag reader is mounted to a support which is provided to adjust said tag reader so as to bring it in alignment to at least one of the tags so as to enable said tag reader to read said tag, wherein said support may be provided to adjust the distance of said tag reader to said medication reservoir, wherein said tag reader may comprise a camera adapted to read the tags which preferably are provided as barcodes, wherein said tag reader may further comprise at least one mirror and an adjustment equipment adapted to adjust the viewing angle and/or the position, in particular the height, of said mirror relative to both said tags so as to enable the camera to read said tags, in particular essentially in the same perspective and/or in the same viewing window.

According to a still further preferred embodiment, the infusion equipment includes the tag reader and is part of the claimed device.

According to a modification of the aforementioned embodiment, said infusion equipment includes a, preferably consumable, pump mechanism unit.

According to an alternative modification of the aforementioned embodiment, said infusion equipment includes an infusion pump comprising a, preferably consumable, first part which includes a pump mechanism and is provided with the inlet port, and a second part including said tag reader and a motor for driving the pump mechanism of the first part, wherein the first part is reasonably attachable to the second part for operation of the infusion pump.

Preferably, the infusion equipment comprises a flow sensor and detector which includes said tag reader.

According to a further preferred embodiment, said first tag is provided to store and indicate characteristics of a diluter and said second tag is provided to store and indicate characteristics of a diluent.

According to a further preferred embodiment, there is provided a processing unit adapted to receive from a remote server data, like drug library information, infusion protocol and infusion limits, and to process said data in accordance with the information read from said tags, wherein said processing unit may be further adapted to calculate the concentration of a diluter contained in said medication reservoir and a diluent to be taken from the vessel by using the reading information obtained by the tag reader after having read the tags, wherein preferably said processing unit is further adapted to start with said calculation in accordance with the start of the reading operation of the tag reader, wherein said processing unit may comprise a user interface adapted to output questions asking how many vessels have been used for preparing an admixture.

According to a further preferred embodiment, said medication reservoir further comprises a third port adapted to be coupled to an output port of a further appliance, preferably a syringe.

Preferably, said tag reader is further adapted to read a patient tag.

According to a still further preferred embodiment, said second tag support is adapted to support a second tag which comprises a portion provided to be fixedly attached to a carrier substrate and to be cut through when the second tag is removed from the carrier substrate and attached to said second tag support.

According to a third aspect of the present invention, there is provided a tag to be attached to a medication container, like a medication reservoir or a vessel, at a position where it can be read by a tag reader, comprising a portion, which is provided to be fixedly attached to a carrier substrate and to be cut through when the tag is removed from said carrier substrate.

The aforementioned and other advantages of the present invention will become apparent from the following more detailed description when taken in conjunction with the accompanying drawings of illustrative embodiments.

DESCRIPTION OF PREFERRED EMBODIMENTS

Figure 1A:
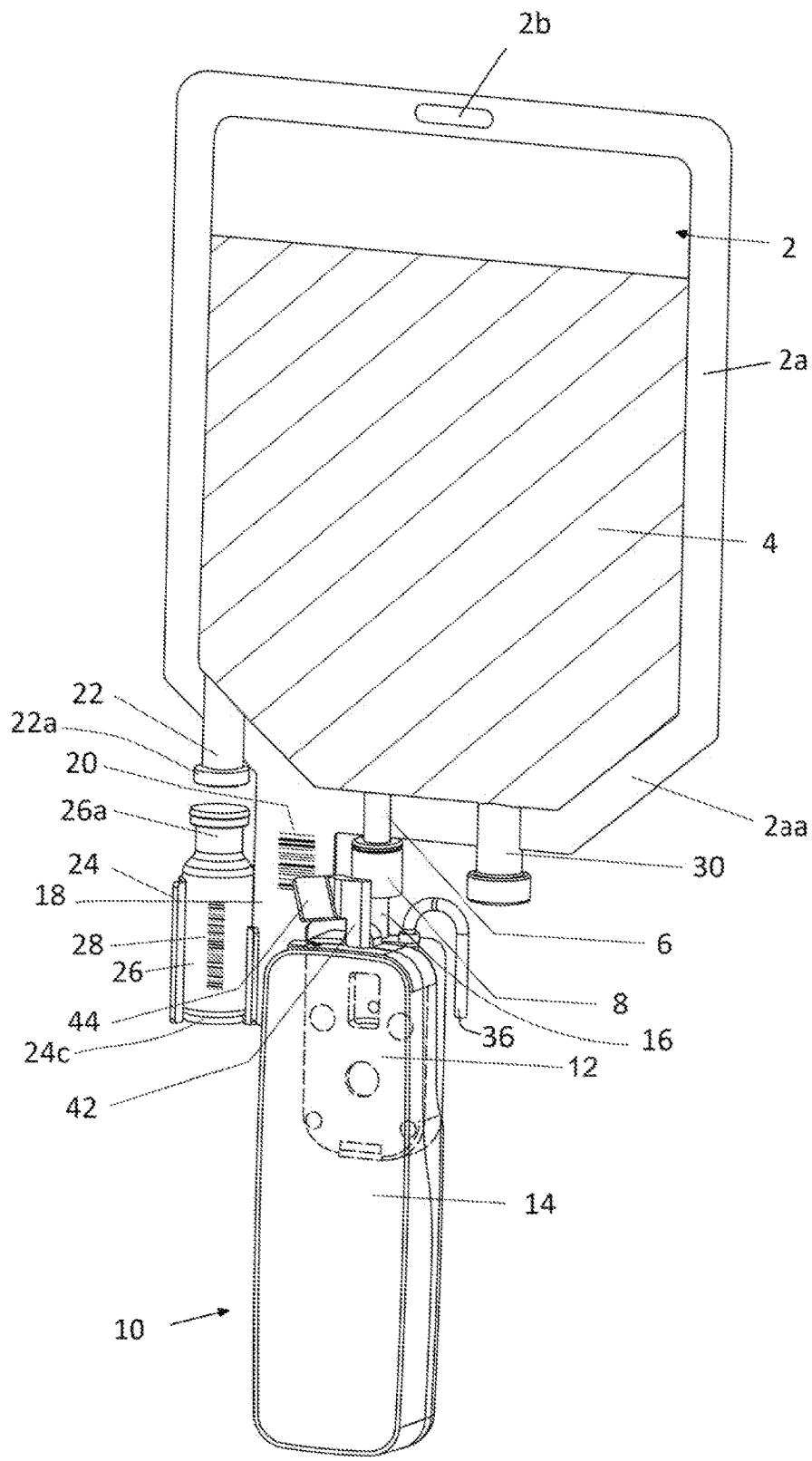
FIG. 1a shows an arrangement of a medication reservoir, an infusion pump and a vessel holder holding a vessel, according to a first preferred embodiment of the present invention.

FIG. 1a shows a preferred embodiment of an arrangement which forms at least a part of an infusion system and comprises a medication reservoir 2. Preferably, the medication reservoir 2 consists of an essentially transparent plastic bag. In the illustrated preferred embodiment, the medication reservoir 2 is bounded by a surrounding edge 2a. The upper portion of the edge 2a of the medication reservoir includes a hole 2b which is provided for attachment of the medication reservoir at a pole (not shown) in its operational mode. FIG. 1a shows the medication reservoir 2 in an orientation which it has in its operational mode.

The reference numeral "4" denotes the content of the medication reservoir 2 which content is a fluid or liquid which preferably in the present case comprises a diluter solution. At its lower edge portion 2aa, the medication reservoir 2 is provided with an outlet port 6 facing downwards. In the illustrated embodiment, the outlet port 6 is formed by a short tube having a connector 8 at its end. The connector 8 may be a luer lock connector. The outlet port 6 is provided to be coupled to an infusion equipment or set comprising an infusion pump 10 as shown in FIG. 1a so as to lead the content 4 of the medication reservoir 2 into the infusion pump 10.

Figure 2A:
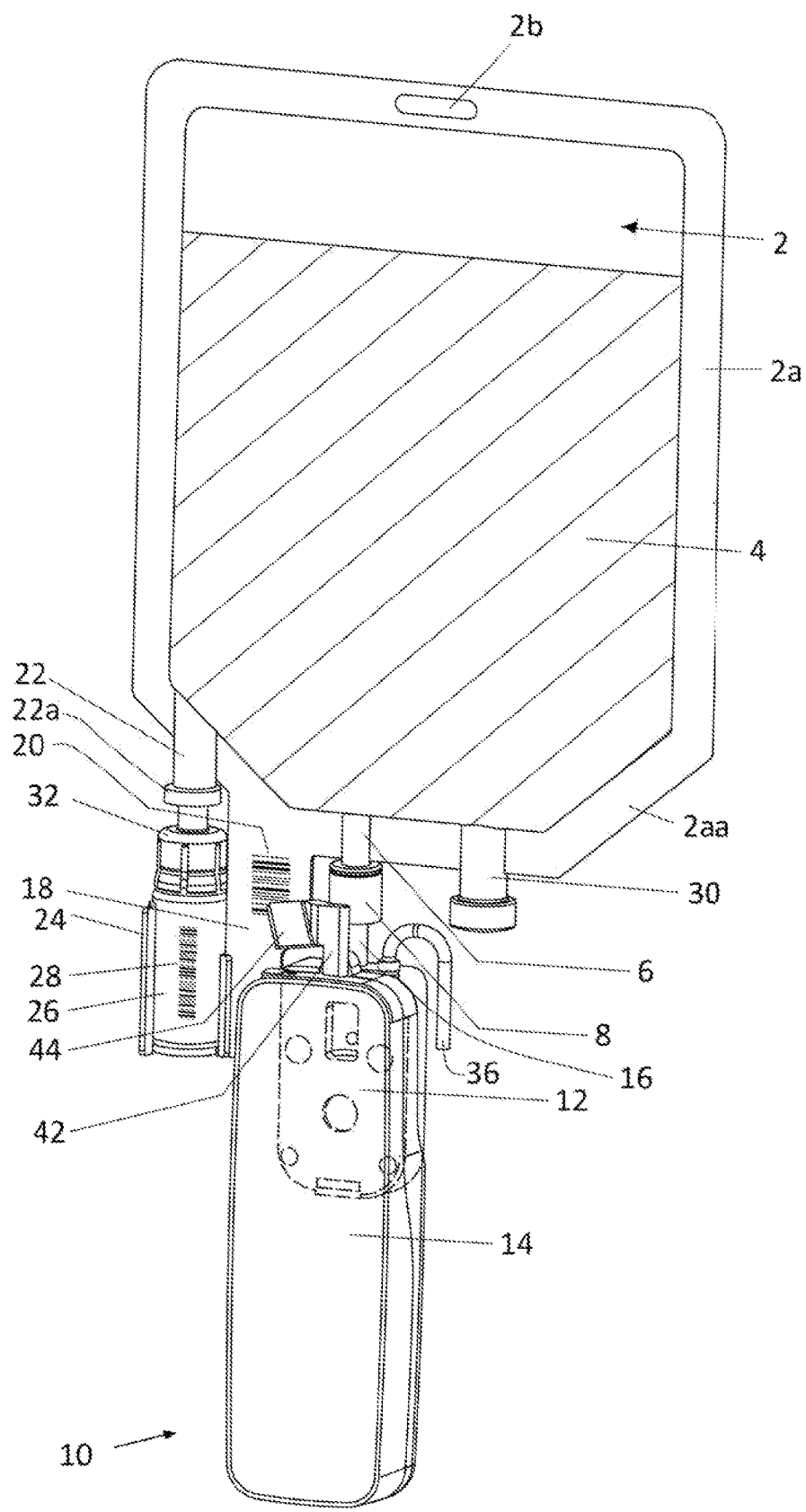
FIG. 2a shows an arrangement of a medication reservoir, an infusion pump and a vessel holder holding a vessel, according to a second preferred embodiment of the present invention.
Figure 2B:
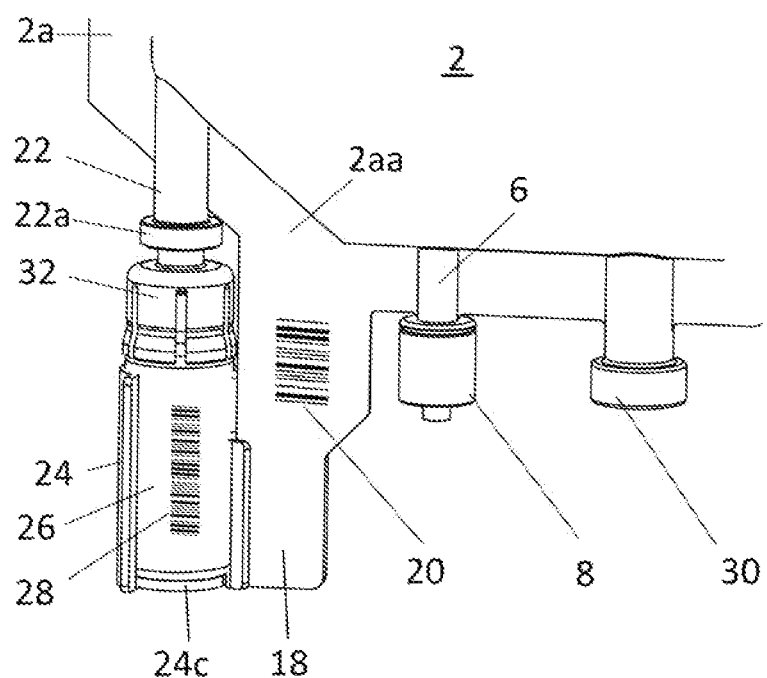
FIG. 2b shows a part of the arrangement of FIG. 2a at the lower edge of the medication reservoir with the vessel held by the vessel holder.

In the exemplary illustration of FIG. 1a, the infusion pump 10 is embodied as a pocket sized or miniature pump. The preferred embodiment of the infusion pump 10 shown in FIGS. 1a and 2a and 2b is divided into two parts, i.e. a first part 12 including a pump mechanism being in particular a rotary peristaltic pump mechanism (not shown) and a second part 14 only including a motor for driving the pump mechanism in the first part 12 and further hardware like control and detection electronics and battery (not shown). According to the shown embodiment, the first part 12 defines a consumable pump cartridge which is preferably made of plastic resulting in low weight and low manufacturing costs. The second part 14 defines the rest of the infusion pump 10 in the shown embodiment and can also be called a pump module. The pump module 14 has also an extremely low weight and a very small size so that it is usually not bigger than drip sensors of today's bedside pumps resulting in an extreme easiness of use. The first part or pump cartridge 12 and the second part or pump module 14 are provided with attachment means (not shown) so as to be able to be attached to each other in order to commonly provide the complete infusion pump 10, wherein the pump cartridge 12 is arranged at the rear side of the pump module 14 so as to create a coupling between the motor (not shown) in the pump module 14 and the pump mechanism (not shown) in the pump cartridge 12.

For pumping the content 4 out of the medication reservoir 2, the pump cartridge 12 comprises an inlet port 16 which is coupled via the connector 8 to the outlet port 6 of the medication reservoir 2. The coupling of the inlet port 16 of the pump cartridge 12 to the outlet port 6 of the medication reservoir 2 results not only in a fluid communication between the medication reservoir 2 and the pump mechanism of the pump cartridge 12 but in the illustrated preferred embodiment also to an attachment of the infusion pump 10 at the medication reservoir 2 so that the infusion pump 10 hangs down from the medication reservoir 2 when the whole arrangement shown in FIG. 1a is in its operational mode. In order to achieve this, the pump cartridge 12 with its inlet port 16 is attached via the connector 8 to the outlet port 6 of the medication reservoir 2 and the pump module 14 is attached at the pump cartridge 12. Whereas the pump cartridge 12 forms a consumable component which is usually disposed after having been used, the pump module 14 is reusable so as to be combined with further pump cartridges. According to the exemplary illustration of FIG. 1a, the infusion pump 10 has an elongated shape with an upper end face defining the upper end of the infusion pump 10 and facing to the lower edged portion 2aa of the medication reservoir 2 in its operational mode shown in FIG. 1a wherein a portion of the end face of the infusion pump 10 is formed by a corresponding portion of the pump cartridge 12 which is provided with the inlet port 16. In the illustrated preferred embodiment, the inlet port 16 is formed by a short tube extending away from the upper end face of the infusion pump 10.

In the preferred embodiment shown in FIG. 1a, the medication reservoir 2 is further provided with a protrusion 18 which is suspended or hangs down from the lower edge portion 2aa of the medication reservoir. The protrusion 18 has a flat, sheet or plate like shape and preferably is provided as a flap forming a single-piece with the medication reservoir 2 and in this case made of the same material as the medication reservoir 2. As further shown in FIGS. 1a to 1c, the protrusion 18 is provided with a medication reservoir tag 20. This tag 20 includes information about the content 4 which has been originally given into the medication reservoir 2 and with which the medication reservoir 2 has been delivered before the content 4 will be mixed with an additional medical substance to be given into the medication reservoir 2. As already mentioned above, preferably the original content 4 is a dilutor solution whose information is stored in the tag 20. This medication reservoir tag 20 can be provided at the protrusion 18 on several different ways, for example by printing or adhesive bonding so that in such a case the protrusion 18 is provided as a medication reservoir tag support or a portion of the protrusion 18 is provided as a medication reservoir tag support portion. Alternatively the protrusion 18 can be provided as a medication reservoir tag support which does not form a single piece with the medication reservoir 2 but is a separate piece which is to be attached, for example by adhesive or thermal bonding, at the lower edge portion 2aa at the medication reservoir 2.

Figure 1B:
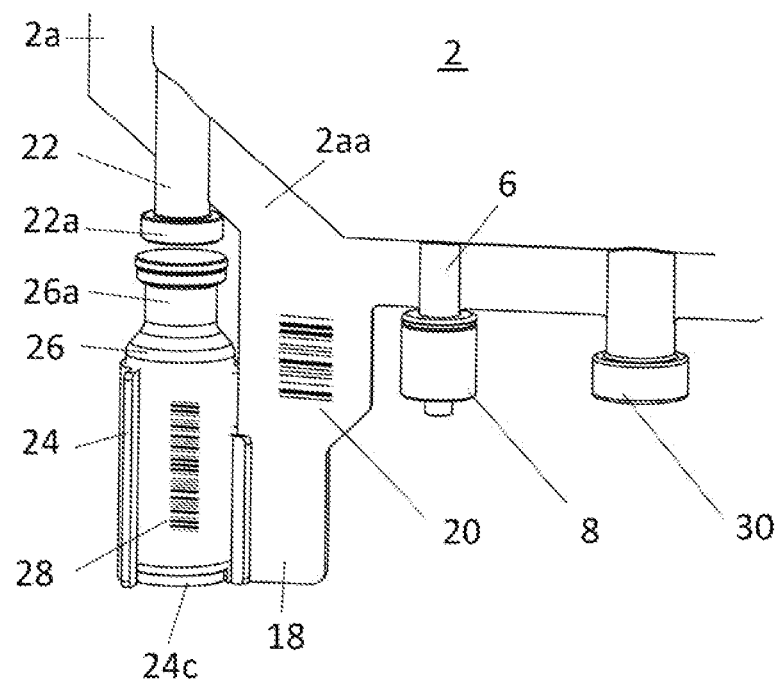
FIG. 1b shows a part of the arrangement of FIG. 1a at the lower edge of the medication reservoir with the vessel held by the vessel holder.
Figure 1C:
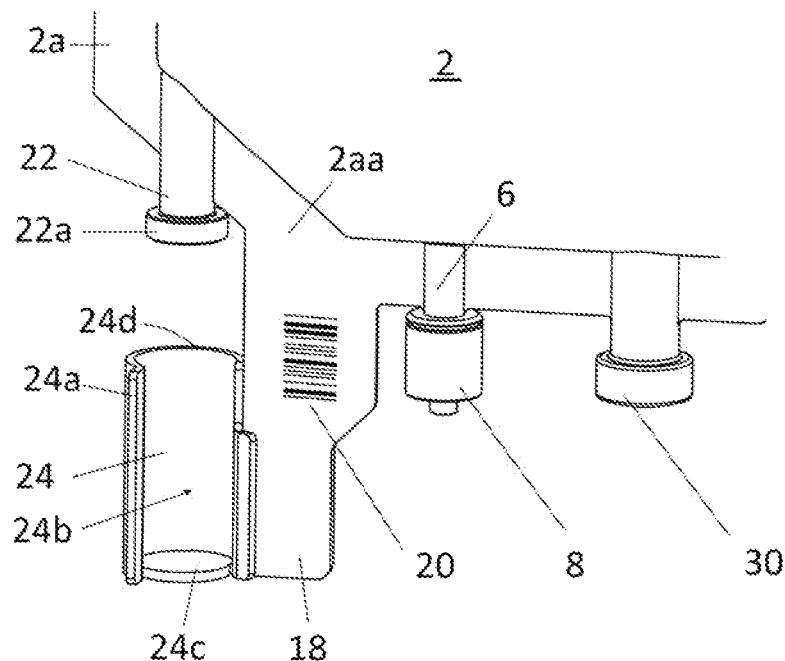
FIG. 1c is the same illustration as FIG. 1b, but with a vessel being removed.

In the preferred embodiment shown in FIGS. 1a to 1c, the medication reservoir 2 is provided with a vessel port 22. According to the exemplary illustration of FIG. 1a, this vessel port 22 is formed as a short tube whose end comprises a cap 22a. A vessel holder 24 is arranged at the protrusion 18 and provided for holding a separate vessel 26. This separate vessel 26 includes an additional medical substance, preferably a diluent. The opening 26a of the vessel 26 is closed when the vessel 26 is filled with the additional medical substance and delivered before use. The vessel port 22 and its cap 22a as well as the opening 26a of the vessel 26 are adapted such that they can be connected to each other with the cap 22a of the vessel port 22 and the opening 26a of the vessel 26 being opened. By doing so, a fluid communication between the vessel 26 and the medication reservoir 2 is created in order to transfer the additional medical substance from the vessel 26 into the medication reservoir 2 for preparing an admixture in the medication reservoir 2. This can be done preferably before the infusion pump 10 will be coupled to the outlet port 6 of the medication reservoir 2 and before the vessel 26 will be brought into holding engagement with the vessel holder 24 wherein the medication reservoir 2 only with the vessel 26 connected to the vessel port 22 is turned upside down in order to fill the additional medical substance from the vessel 26 into the medication reservoir 2. Alternatively it is also possible to turn the medication reservoir 2 with the vessel 26 connected to the vessel port 22 of the medication reservoir 2 and with the infusion pump 10 already connected to the outlet port 6 of the medication reservoir and/or with the vessel 26 already engaged by the vessel holder 24. After the vessel 26 has been emptied, the cap 22a of the vessel port 22 is closed again in order to avoid any leakage of the admixture out of the medication reservoir 2.

If not done before, the vessel 26 is brought into holding engagement with the vessel holder 24 as shown in the FIGS. 1a and 1b wherein in the embodiment shown the holding engagement is done by clamping.

As further shown in the FIGS. 1a and 1b, the vessel holder 24 is preferably embodied to hold a small bottle or vial as separate vessel 26. As it further becomes clear from the FIGS. 1a to 1c, the vessel port 22 at the medication reservoir 2 is arranged adjacent to the vessel holder 24, but in such a distance thereto that there is enough space which allows attachment of the vessel 26 to the vessel holder 24 and detachment of the vessel 26 from the vessel holder 24. Further, as shown in the FIGS. 1a and 1b, the vessel port 22 and the vessel holder 24 are arranged relative to each other so that the vessel port 22 essentially faces the opening 26a of the vessel 26 when the vessel 26 is attached to the vessel holder 24. Moreover, the vessel holder 24 is provided to hold the vessel 26 in an essentially vertical orientation with its opening 26a facing upwards when the arrangement shown in FIG. 1a is in its operational mode.

As it in particular becomes clear from FIG. 1c which shows the vessel holder 24 without the vessel 26 being attached thereto, in the exemplarily illustrated preferred embodiment, the vessel holder 24 comprises a hollow body 24a having a curved shape along its whole length oriented in vertical direction when the arrangement of FIG. 1a is in its operational mode, and including an opening 24b along the whole length of the vessel holder 24. Alternatively, it is conceivable to provide a window in the wall of the hollow body 24a instead of providing the opening 24b extending along the whole length of the vessel holder 24 wherein such a window might be provided as a so-called axis or passage orifice or be closed by a transparent material. According to the preferred embodiment, the hollow body 24a of the vessel holder 24 has a tubular shape with an essentially "Ω"-like cross section wherein the opening 24b extends over an angular range less than 180 degrees, preferably about 150 degrees, in the cross section plane. Further, the hollow body 24a is made of elastic material, in particular plastic material, at least in its portions bounding the opening 24b so as to enable the vessel 26 to be inserted sidewardly through the opening 24b into the hollow body 24a and then to be hold in the hollow body 24a of the vessel holder 24 by clamping effect.

The hollow body 24a is closed at its lower end by a bottom plate 24c as in particular apparent from FIG. 1c so that the bottom of the vessel 26 when accommodated in the hollow body 24a abuts the bottom plate of the hollow body 24a of the vessel holder 24 as shown in the FIGS. 1a and 1b. Further, the hollow body 24a is open at its upper end 24d which faces the vessel port 22 of the medication reservoir 2 and is hence adjacent to it as in particular apparent from FIG. 1c so as to enable the vessel 26 when attached to the vessel holder 24 to face its opening 26a to the vessel port 22 as shown in FIGS. 1a and 1b.

As it become also apparent from the FIGS. 1a and 1b, the used vessel 26 is provided at its outer surface with a vessel tag 28 which stores information about the additional medical substance which has been originally included in the vessel 26 before the vessel 26 is emptied into the medication reservoir 2 for preparing an admixture therein. Not only for a general documentation purposes but also for reading to be described thereafter in detail, the empty vessel 26 is removably attached to the vessel holder 24 by orientating its vessel tag 28 so as to be exposed within the opening 24b of the hollow body 24a of the vessel holder 24 as illustrated in the FIGS. 1a and 1b, so that in such a case the vessel holder 24 takes up the tasks of the vessel tag support.

According to the preferred embodiment shown in the FIGS. 1a to 1c, the medication reservoir 2 is further provided with a third port 30 which is adapted to be coupled to an output port of a further appliance, preferably a syringe (not shown). However, alternatively this third port can also be omitted if not needed.

FIGS. 2a and 2b show a further preferred embodiment which only differs from the preferred embodiment according to the FIGS. 1a and 1b in that the opening of the vessel 26 has an elastic tap whereas a plastic fluid transfer connector 32 is provided as a dual spike cap whose dual spike (not shown) penetrates into the vessel port 22 of the medication reservoir 2 upwards and into a rubber top of the vessel 26 downwards for creating a fluid communication between the vessel 26 and the medication reservoir 2 so as to prepare an admixture. After the additional medical substance has been transferred from the vessel 26 into the medication reservoir 2 wherein preferably the vessel 26 as already brought into holding engagement with the vessel holder 24 before, then the said dual spike can be kept in place or removed—provided the vessel 26 is arranged in the vessel holder 24 so that the vessel tag 28 is exposed as described above.

Figure 3:
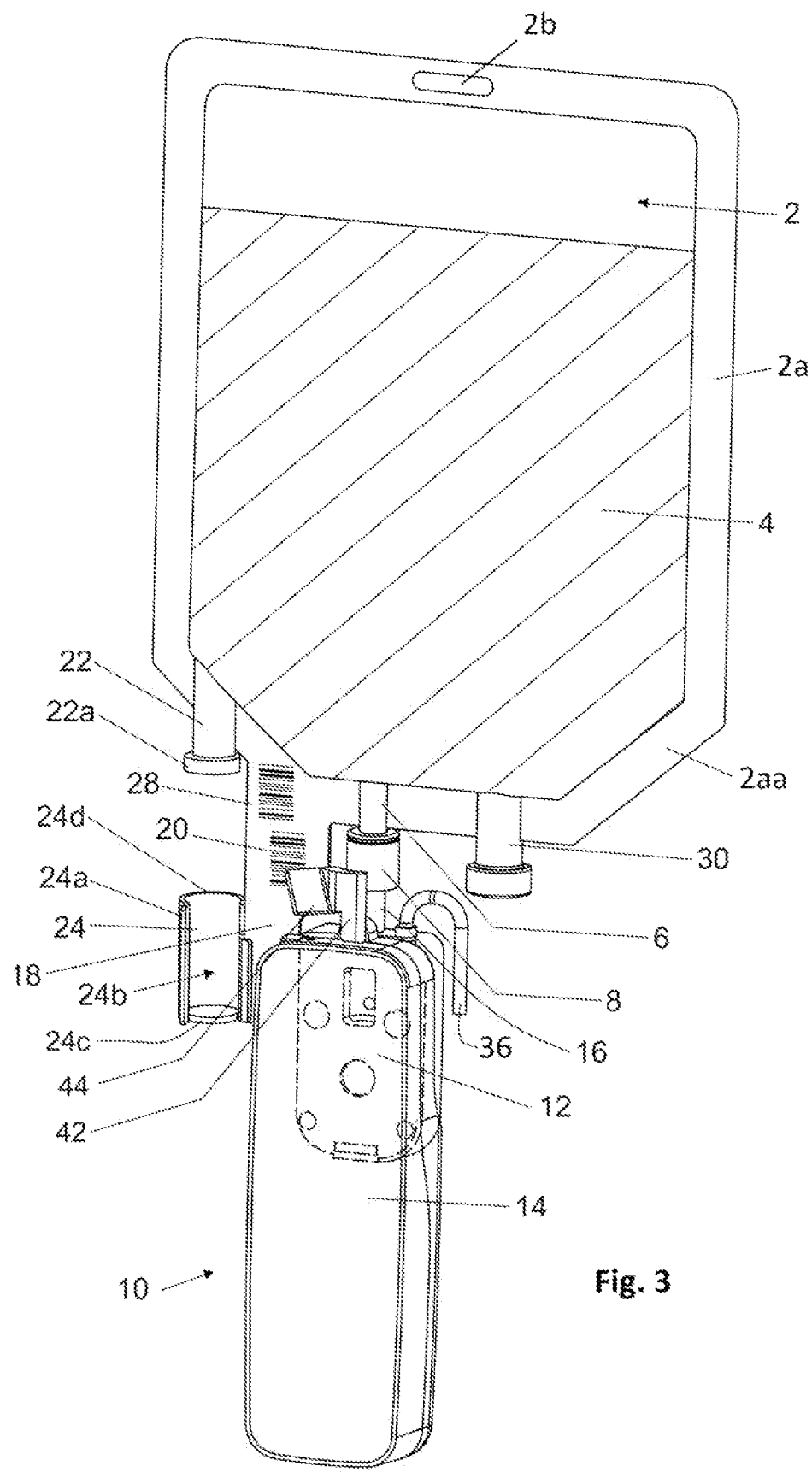
FIG. 3 shows an arrangement of a medication reservoir, an infusion pump and a vessel holder, according to a third preferred embodiment of the present invention.

FIG. 3 shows a further preferred embodiment which differs from the embodiments shown in FIGS. 1 and 2 in that the protrusion 18 is provided not only with the medication reservoir tag 20 but also additionally with the vessel tag 28 so that the protrusion 18 comprises a first tag support portion carrying the medication reservoir tag 20 and a second tag support portion carrying the vessel tag 28 and, hence, forms a common tag support for both the tags 20, 28 wherein both the tag support portions are arranged close to each other. Preferably, the medication reservoir tag 20 is fixedly arranged at the protrusion 18, in particular by printing or fixedly attaching, and the vessel tag 28 is provided as a self-adhesive sticker which is originally attached at the vessel or its package and for preparing the admixture in the medication reservoir released from the vessel or its package and arranged at the protrusion 18. Although in this preferred embodiment the vessel holder 24 is still provided for holding a vessel like the vessel 26 shown in the FIGS. 1a and 1c as well as 2a and 2b, it is not needed to place the vessel in the vessel holder 24 so as to expose its vessel tag, if there is still any, for orientation to the mirror 44, but the vessel holder 24 is only used for keeping the empty vessel.

Figure 4:
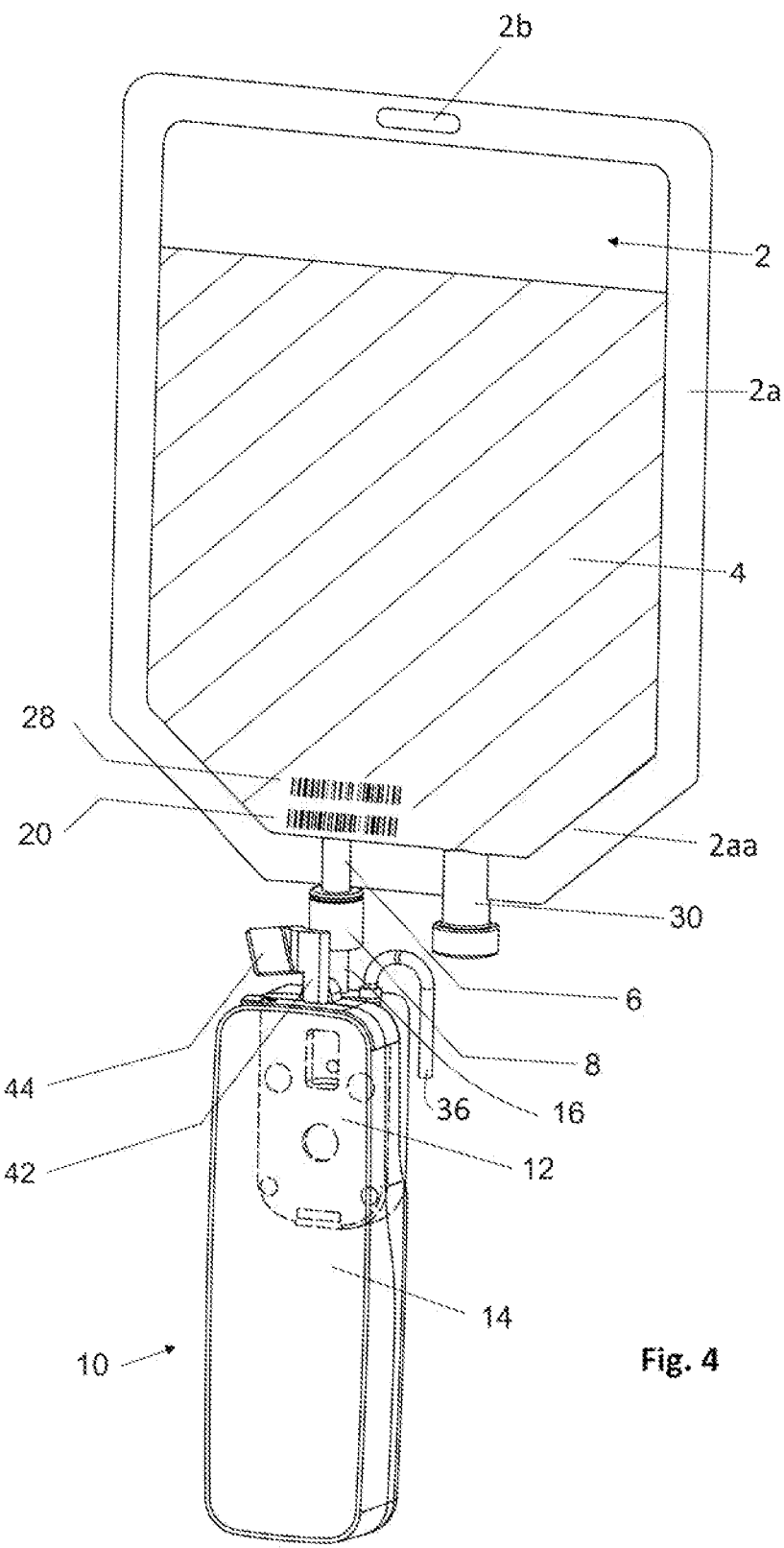
FIG. 4 shows an arrangement of a medication reservoir and an infusion pump, according to a fourth preferred embodiment of the present invention.

FIG. 4 shows a further preferred embodiment which differs from the embodiment of FIG. 3 in that both the protrusion 18 and the vessel holder 24 are not provided and both the medication reservoir tag 20 and the vessel tag 28 are attached at the medication reservoir 2 or at its lower edge portion 2aa, whereas the attachment of both the tags 20, 28 is preferably done in a similar or same manner as described in conjunction with the embodiment of FIG. 3. So, a first portion of the medication reservoir 2 forms a first tag support portion for the medication reservoir tag 20 and a second portion of the medication reservoir 2 forms a second tag support portion for the vessel tag 28 so that the medication reservoir 2 itself is provided as a tag support. As also apparent from FIG. 4, both the tags 20, 28 should preferably be arranged close to each other and close to the outlet port 6 and, hence, to the lower edge portion 2aa of the medication reservoir 2. In the preferred embodiment of FIG. 4, the vessel (not shown here) with its opening is to be temporarily connected to the port 30 for transferring the additional medical substance from the vessel into the medication reservoir 2 so as to prepare the admixture, so that this port 30 take up the function of the inlet port 22 of the embodiments of FIGS. 1, 2 and 3 which inlet port is hence not provided in the embodiment of FIG. 4 as well. In a further embodiment, the empty vessel 26 can be stored after dilution in a plastic pocket which is made preferably from the same material as the medication reservoir and is arranged with its three side and lower edges at the medication reservoir 2 usually by thermal bonding. This pocket is transparent, so that the vessel tag 28 of the vessel 26 stored therein can be read from its front face simultaneously with the medication tag 20. So, in the embodiment of FIG. 4 the port for connecting a vessel can be basically provided at any point of the medication reservoir 2.

Figure 5:
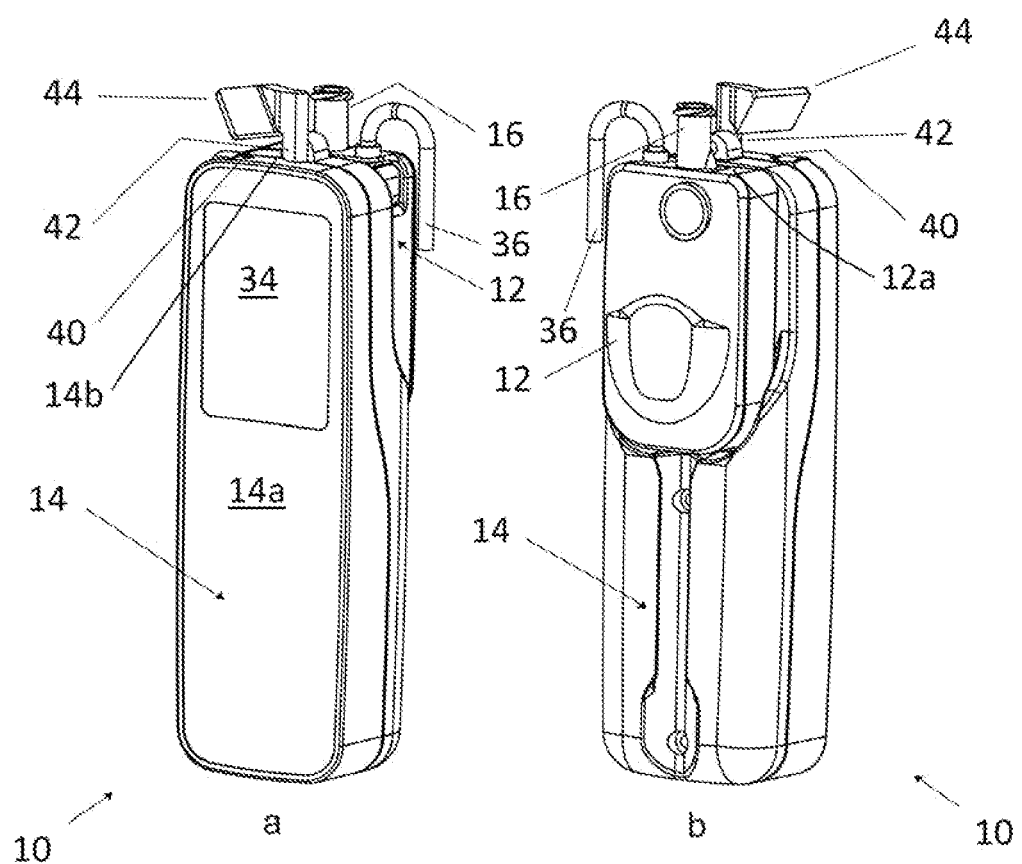
FIG. 5 shows a preferred embodiment of the infusion pump (equipment) in a perspective front view (a) and a perspective rear view (b).

FIG. 5 is a more detailed illustration of the infusion equipment including the infusion pump 10 and an infusion set as used in the preferred embodiments described herein.

In addition to the description of the infusion pump 10 already given above, as become apparent from FIG. 5a, the front face 14a of the pump module 14 comprises a display 34, wherein the portion of the front face 14a of the pump module 14 below the display 34 can be provided e.g. with the buttons (not shown). As further apparent from FIG. 5 and also from the FIGS. 1a, 2a, 3 and 4, an outlet tube 36 is schematically shown which is connected to the pump cartridge 12, so that the pump cartridge 12 pumps the admixture from the medication reservoir 2 through its inlet port 16 to the outlet tube 36. Further, it is more apparent from FIG. 5b that according to the exemplarily illustrated preferred embodiment the input port 16 is placed at the top 12a of the pump cartridge 12 and is provided with a female luer connector which is to be brought in screwing engagement with the connector 8 shown in FIGS. 1 and 2 and provided as a male luer connector in such a case.

In order to read both the tags 20 and 28, there is provided a tag reader which according to the exemplarily illustrated embodiments described herein comprise a camera 40, a mirror stem 42 and a mirror 44. The pump module 14 includes the camera 40 which is placed such that the camera 40 faces from the top 14b of the pump module 14 upwards. The mirror stem 42 is arranged adjacent to the camera 40 at the top 14b of the pump module 14 so as to protrude from the top 14b and carries at its upper end the mirror 44. The mirror 44 at the upper end of the mirror stem 42 is arranged and oriented relative to the camera 40 on the one hand and to both the tags 20, 28 on the other hand so that the camera 40 is able to read both the tags 20, 28 at the same time in the same perspective and/or in the same viewing window. In order to achieve this, both the tags 20, 28 are to be placed close to each other as apparent from the FIGS. 1a, 1b, 2a and 2b, 3 and 4. In order to exactly adjust the orientation of the view to both the tags 20, 28, the mirror stem 42 is preferably variable in its height and/or pivotable and/or rotatable around its own longitudinal axis so as to adjust its turning position, so that with this preferred embodiment the mirror stem 42 forms an adjustment means or is at least part thereof. Further, the mirror stem 42 is preferably foldable and unfoldable and/or pivotable between a resting position and an operational position. The camera itself nowadays being exceedingly small in dimensions can also be placed on an edge or top of the mirror stem 42 which preferably comprises also adjustment means for the viewing direction.

Moreover, in the preferred embodiments according to the FIGS. 1a to 1c, 2a and 2b and 3 the vessel holder 24 is arranged at the protrusion 18 which again is placed close to the outlet port 6 of the medication reservoir where the infusion pump 10 with its pump cartridge 12 is to be attached. Nevertheless, it is also conceivable in principle to arrange the vessel holder 24 at a different place rather than at the protrusion 18, for example at a different portion of the medication reservoir or at a stand-alone support provided separately from the medication reservoir 2, and/or to provide as a separate unit. Further, it is also conceivable to arrange the protrusion 18 with the medication tag 20 at a portion of the medication reservoir 2 different from the lower edge portion 2aa provided both tags 20, 28 remain visible by the mirror 44 (which in this case must have an orientation different from that shown in the Figures) at the same time and in the same perspective and/or in the same viewing window. Moreover, whereas the vessel holder 24 according to the preferred embodiments shown in the FIGS. 1a to 1c, 2a and 2b and 3 is provided to hold the vessel 26 by a clamping effect and, hence, its body 24a is essentially more or less rigid, alternatively the vessel holder can be provided as a pocket or bag which comprises a window or is at least partly made of transparent material which is preferably the same material as that of the medication reservoir 2.

As mentioned above, in the illustrated embodiments the camera 40, the mirror stem 42 and the mirror 44 form or are at least parts of the tag reader which again is part of the pump module 14 and, hence, of the infusion pump 10. However, it is also conceivable to incorporate the components necessary for forming the tag reader into a flow sensor or a flow detector, if the use of a flow sensor and/or a flow detector is needed whereas the flow sensor is provided at the consumable pump cartridge 12 and the flow detector at a non-disposable infusion equipment like the pump module 14 combined with tag reader. Also it is alternatively conceivable implement the tag reader as a stand-alone unit to be provided separately from the infusion pump 10 and/or from other components of the infusion system to be used and preferably to be attached to the outlet port 6 of the medication reservoir 2.

The tag reader as described in conjunction with the illustrated embodiments operates on an optical basis so that the tags 20 and 28 are formed as optically readable tags, preferably barcode labels (linear or QR) as apparent from the FIGS. 1a to 1c, 2a and 2b, 3 and 4. However, it is also conceivable to provide the tags as RFID tags and the tag reader as an electronic device adapted to read said RFID tags.

In the following the above description of the preferred embodiments are supplemented by additional descriptions, wherein the same reference numerals as used above and given in the figures are normally used for designation of the same components as described above, even though a different name is given for some of these components in some cases in particular if such components are provided according to a more or less different embodiment.

The medication reservoir 2 can be prefilled or sold as empty reservoir to compounding units or hospital pharmacies. In such a case a barcode 20 is placed by the pharmacy/compounder.

The pump cartridge 12 that is snap fitted on the back of the pump module 14 is connected fluidly and mechanically with (hanging from) the outlet port 6 through its upper tube 16 with a female connector 8 screwed onto the infusion port 6 which is embodied as a male connector so that the whole infusion pump 10 is infusing and mechanically hold in position.

The camera 40 on top of the pump 10 with a lever 42 to elevate an inclined mirror 44 as a periscope can take a picture of both the barcode 20 and the barcode 28 so as to deduct the admixture concentration from the diluter volume and diluent mass. The reading can also be done not automatically but manually, wherein the user points the camera 40 to one and the other tags for manual reading, and after this process the infusion pump allows the infusion if the result of the calculation of the drug and dilution matches the associated protocol.

FIG. 2a shows a dual spike vial cap 22a that penetrates into a reservoir dilution tube 22 upwards and into an elastic cap 32 downwards for preparing an admixture. Normally, a powder lyophilized drug receives a diluter from reservoir 2, and then the user turns the system upside down in order to transfer the dilution into the reservoir 2 by gravity. Then the dual spike can be kept in place or removed provided that the barcode 28 is placed in front so to be visible from the camera 40.

FIG. 1c is a detail that shows the lower part of the reservoir 2 with the drug vial holder 24 preferably as a semi rigid receptacle in form of an "Ω" that by means of spring action opens and then holds the vial 26 securely in place and orientation by exposing the barcode 28 so as to make it visible to the camera 40 and the mirror 44. This is the reservoir 2 as sold before admixture. The tube 22 can be higher as in this preferred embodiment because it does not need to get fluid from the bottom of the reservoir 2 during the admixture process.

FIG. 1*b* shows the same with the vial 26 filled before the admixture and secured in place for transport to patient or after admixture for documentation and safe dilution calculation and pump programming.

FIG. 2*b* shows the same with the dual spike elastic cap 32 not removed.

FIG. 5 shows the pump 10 comprising a mechanism cartridge 12 with an upper tube 16 having a female luer connector, a camera 40, a mirror stem 42 and a mirror 44.

In a preferred embodiment, the pump 10 has a cartridge 12 that has an inlet port 16 and output tubing 36; but a more conventional pump without such a cartridge can also be used. The cartridge 12 is snap fitted on the pump and securely holds the pump 10 when connected to the outlet port 6 of the medication reservoir 2.

A preferred process of an error free fully automatic infusion of admixture can be as follows:

1) The nurse gets five parts: The reservoir 2 with a diluter 4, the drug vial, the pump cartridge (infusion set) 12, the pump module 14, and admixture dual spike with flexible cap 32, all of which can be delivered from a hospital pharmacy.
2) She mixes the diluter fluid 4 in the reservoir 2 with the drug from the vial 26 usually using the dual spike flexible cap 32 as known in the art.
3) The empty vial 26 is put in the holder cavity 24*b* below the reservoir 2 with its barcode 28 readable by the pump wherein the dual spike connector 32 can be kept or removed.
4) The cartridge 12 is connected to the reservoir 2 by means of a swabable needle-free valve of a luer lock connector or by means of a standard luer lock connector 8 which all can hold the cartridge 12 and the pump in place.
5) Gravity prime infusion set.
6) The nurse points the pump 10 to a patient and scans a patient barcode bracelet by the pump's camera 40.
7) The pump is connected to the cartridge 12 so that the pump through the connector 8, hangs from the outlet port 6 of the medication reservoir 2, wherein further the camera stylus 42 is pivoted to its upper position so that with its inclined mirror 44 the camera 40 on top can read both barcodes 20 and 28, wherein alternatively the mirror 44 can also be placed very close to the camera 40 without stylus 42.
8) Then, the pump 10 automatically scans both the diluter and diluent barcodes 20, 28 readable from the camera 40 below, finds from a downloaded drug library the volume of each admixture and the drug mass and calculates the admixture concentration
9) The pump 10 from an interoperability communication asks the hospital system for a correct protocol for the scanned patient and drug admixture in order to avoid delivery of a wrong medication at wrong time to wrong patient
10) The pump 10 validates that the received protocol is valid for the read admixture and concentration and, if so, the pump is self-programming and allows start of the infusion after confirmation from the nurse.
11) The nurse starts the infusion on the pump.
12) If during the infusion the reservoir 2 or vial 26 is changed, a new scan will be done automatically and new reservoir contents will be read with giving a warning to the nurse and checked again with the interoperability systems so that medication errors are prevented.
13) Several infusions can be made by the same infusion set reading different reservoirs, and the pump 10 can infuse them all with one battery charge, as many as needed for all days a patient stays at the hospital (usually 4 days and 7 litters fluids). The preferably swabable needle-free connector 8 helps during change from reservoir to reservoir to reduce or eliminate contamination of the infusion line.

The present invention provides a novel drug reservoir to facilitate the process and make the drug admixture infusion as prefilled or empty for compounding safer. The reservoir 2 preferably provides a connecting tubing for an infusion pump set with a male luer lock connector 6 on the reservoir 2, while the pump infusion set has a female swabable needle-free connector 6 that opens by connecting to a reservoir's male luer. This allows patients to connect with one infusion set to several reservoirs with low contamination risk thanks to a swabable connection so that one pump can follow the patient at his different locations in the hospital as a new paradigm compared to today's stationary pumps at each location. For this paradigm, a luer lock connection allows a miniature infusion pump 10 to hang from the reservoir 2 safely in addition to its weight whatever lightweight it can be. Of course, standard spike connection as usual is possible preferably using a pump provided spring clamp-clothespin over the connector 16 for holding the pump weight. The reservoir 2 also in addition is provided with a tag 20 that can automatically be read by the fluidly connected infusion pump system (through its infusion set) directly or in proximity (at reading distance). The reservoir 2 also in addition provides a holder or safe receptacle 24 for the drug vial 26 labeled with a tag 28 for an admixture process, in a way that it also can be read by the camera 40 being part of a tag reader which in particular is provided in or at an infusion pump or a flow sensor. The receptacle 24 preferably is a semi-rigid "Ω" shaped holder that engages the vial 26 and keeps it safe at transport or use, while having its face to the pump side open so that its tags 28 can be read when the vial 26 is inserted and hold by spring action of the "Ω" flags. This way the pump system can read both diluent and diluter tags 20, 28 and calculate the concentration of the admixture, and allow or not the start of an infusion, if the patient name and the prescription match or not the drug name and concentration of admixture, so as to prevent human medication errors. The vial 26 can be carried by the holder 24 arranged at the diluter reservoir 2 before carrying out the admixture (FIG. 1*a*/FIG. 2*b*) as well as while empty after mix safely in the receptacle 24. So, the present invention reduces a hand writing of traditional self-adhesive labels for admixtures and manual pump programming so as to avoid errors and waste time and money. Since the dilution calculation is done for the full diluter volume, different volume diluter reservoirs are available. Reading of the barcodes 20, 28 from the drug vial 26 and the reservoir 2 can be done by a special camera image reading software that in a preferred embodiment can mask one barcode while reading the other.

The procedure can preferably be as follows: Check for a tag 20 or 28 in the picture, and, if found one, mask the rest of the image read and store results, then mask this barcode and search the image if a second tag 28 or 20 is present and, if yes, read it and store results. A read tag can be that of a diluter, a drug, a patient, a location or a caregiver. A drug library transferred into a pump memory and interoperability communication from hospital electronic health records can give the match of the just read tag with a drug/solution name and volume as well as patient name while associating a caregiver to the process documentation. The drug library in the present invention distinguishes a premixed drug from a drug in the vial 26 to be mixed before use, so that when scanned in a non-automatic process the pump 10 asks for scanning the diluter, too, to calculate the concentration of the mix. The vial drug data comprise the mass (mg/microgram) of the drug if lyophilized and also its diluter volume (usually 10 or 20 ml) if ready to use. Equally the pump 10 can have an updated patient name associated to an ID No reference database (of the care area using the pump 10) downloaded so as to fast acknowledge patient name from the read ID. When the pump 10 shows the drug mass or the diluent volume, the user can adjust it to a lower value (if diluted in more than one reservoirs) if that is permitted due to the pump configuration, i.e. the hospital safety rules.

Of course, the holder or receptacle 24 can be in a preferred embodiment adaptable to different sizes of the vial 26, for example by means of a telescopic enlarge-shrink way, and also can be made for more than one vials 26 with same or different drugs, and after reading them the software can adjust the concentration for one drug with more than one vial 26 (additional mass) or for different drugs with different concentrations and infusion rates.

In case of using pre-mixed drugs, the pre-mixed drugs are pharmaceutical products packaged in flexible containers-reservoirs with their wall made of plastic material that does not allow evaporation so to retain the concentration stable in time.

They have a barcode 20 printed on the reservoir 2. Preferably, this barcode or a second one is printed close to the lower edge 2a of the medication reservoir 2 and is oriented vertically to the ground or provided on a plate or protrusion 18 that is showing the barcode facing downwards. In the shown embodiment the mirror 44 to divert the view is needed when the camera 40 is facing upwards, whereas in an alternative embodiment no mirror is needed when the barcode faces downwards.

The barcode 20 is placed close to the outlet port 6 which preferably has a connector to connect with infusion set connector. According to a second preferred embodiment not shown, the infusion pump 10 can be hanged from the outlet port 6 and automatically read the label above; the camera can also be held on a higher stem tip above the infusion equipment, with a preferably adjustable direction of the view.

In case of using a drug label to be peeled off from a drug vial, the drugs usually have on their external carton packaging a label tag that is self-adhesive but removable and can be rebounded on the prescription for reimbursement reasons.

According to a further preferred aspect of the present invention, it is used the principle of a removable and re-applicable peel-off tag for a different purpose: For a safe drug delivery and also to assure the patient compliance to the prescription and also for machine proof to reimbursement social security or other authority that the drug has not only been used but delivered by a pump at a certain period of time.

For doing so, the vial tag 28 is a machine readable label peel-off tag provided preferably on the vial 26, ampoule or other primary liquid or lyophilized drug vessel or container, but also possible on the carton packaging box, wherein said tag 28 is removable as it is self-adhesive bonded by special glue that is also biocompatible and allowed to be placed on a collapsible plastic diluent container like the medication reservoir 2 as shown in the figures without contaminating its content.

Since usually premix drugs are few, in most cases the nurses admix a drug from a vial to a diluent solution container usually containing dextrose or sodium chloride or just water for injection; the compound is called admixture. If using a syringe for mixing, for infusion the syringe itself is connected to a syringe pump, or for infusion the reservoir with the admixture is connected to a Large Volume Pump. However, since there is no automatic documentation of the process, errors may happen.

According to the further aspect of the present invention, the peel-off self-adhesive tag, that can be a bar code print, RFID or other, preferably has a narrow stem part of paper to be cut-broken at removal so as to make sure that the label is original from the pharmaceutical company and not placed by a third person's hand accidentally or intentionally.

The reservoir 2 according to a preferred embodiment comprises close to its outlet port 6 a vertical or horizontal plate similar to the protrusion 18 shown in the figures which is provided with the solution tag 20 from where the volume and diluent (dextrose or sodium chloride) of the solution contained in the medication reservoir 2 is read wherein there is a free space adjacent to it for the second tag 28 being said peel off label to be put so that it can be read by the infusion equipment comprising the infusion pump 10 with a reader hanging from the reservoir 2, a more classic pump with a reader proximal at reading distance to both the reservoir and the drug vial, or a flow sensor with a tag reader communicating with a more distant pump. The reservoir 2 can also have a connector as outlet port 6 (instead of a classic tube for spike connection) so as to be connected with the infusion set connector wherein the pump itself can be hanged from the infusion set and the connector so to enable said new treatment and infusion paradigm.

The removed tag 28 is then self-adhesively put close, i.e. in a predefined position, on the medication reservoir 2 used as a dilution container adjacent to its tag 20 or in another embodiment on a plate at the back of the vial receptacle 24 in order to be visible and readable automatically from the pump 10 infusing its contents any time at start or during the infusion without human action. The action is that the pump 10 reads both and makes calculation of the concentration of the mix from the volume and contents of each parts. Two or more labels or tags can be read from the infusion system like additives put in a parenteral nutrition so as to be documented and to assure compliance of the patient to prescription. The process can also be carried out by manually reading the tags in sequence by the pump equipment For doing so, the software of the camera based barcode reader can recognize at least one tag in a picture with its usual scan method, read it as usual, then can paint the picture portion of the read tag (e.g. 20) with white colour and scan again the edited picture to find the second one (e.g. 28). Then it reads it also as usual, and both tag data are processed to find the drug names, volumes and mass so that pump software can calculate the drug concentration in the mix.

The tag 28 which preferably comprises a print removable peel-off cut on the vial 26 in addition to the barcode ID, preferably also electronically indicates the drug name and the mass (mg/μg) of the content ("electronically" means that readable information is preferably possible with square QR barcode tags that may contain lots of information) avoiding the need of a drug library to interpret the ID No. So once replaced over the reservoir mix plate the nurse does not need to write by hand a print label of the mix content. The user can read both the drug and the solution from their respective tags 20 and 28 so that errors in labeling are avoided. The recommendations to the nurses are that they have to extract all content from the drug vial 26 and use it in the mix so that the pump 10 reading both tags 20, 28 can make calculations on the concentration of the mix correctly.

There is a possibility that a portion of the solution before the mix is removed and hence the initial volume is reduced, wherein in such a case there is an option on the pump 10 to reduce the read volume of the solution from the tag 20 to the remaining volume in the reservoir 2 before drug insertion.

The pump system can comprise a pump like the pump 10 shown in the figures and itself hanged from and below the drug container like the medication reservoir 2 shown in the figures or on pole mounted conventional infusion pumps, a reader on top reading the container that is arranged just above the pump in a special vertical or inclined holder, or a flow sensor combined with a tag reader communicating to a distant infusion pump whereby conventional pumps can become safe.

When infusion is finished, the pump 10 sends information feedback to the electronic medical record and to the reimbursement route for compliance and payment.

The invention prevents errors from mixing and delivery, the pump can read the drug label ID No and retrieve the drug name and concentration from the drug library and from the dilution calculation, understand mg or microgram per litter of diluent and allow safe manual programming or automatic programming resulting from interoperability with systems like EPIC or CERNER or electronic medical prescription, once a patient tag is also previously read.

The pump module 14 according to the preferred embodiment shown in the figures is small and lightweight and hanging from a consumable infusion set connected to the reservoir 2 with the premix to be delivered, wherein preferably the consumable infusion set comprises a cartridge 12 that contains the infusion mechanism and a line to the patient and upstream has no tubing but a connector 8, luer or other, according to the type of therapy different for IV, enteral or epidural treatment, that can also be a needle-free connector that protects from infections.

The reservoir 2 containing a drug mix comprises a male connector as outlet port 6 on a connecting tube at its lower end that has the force to hold the weight of the pump module 14 that is attached preferably by snap fit on the consumable cartridge 12, when the outlet port 6 is connected through the connector 8 being a female connector to the cartridge 12 forming the disposable infusion set of the pump 10.

Therefore in a preferred embodiment the female needle-free connector 8 on the upstream side provides a connection with the male outlet port 6 of the drug reservoir 2, wherein the reservoir 2 and the infusion set hangs from a pole, it is preferably gravity primed and the pump module 14 snap fits on the said cartridge 12 so that it safely hangs from the reservoir. The connector 8 can also be no needle-free as a standard luer lock, and also may have for an easier connection a freely rotating collar for the connecting threads and compress the male into female receptacle as known in the art.

The consumable cartridge 12 may have for piggyback infusions a Y or T connector upstream comprising one vertical end with a connector so that all above about automatic tag reading are feasible, whereas the other end has a tubing for secondary or primary reservoir, preferably having a system compatible flow controller (a flow detector with an active valve) with a tag reader integrated which can be mounted higher or lower to the proximal reservoir according to standard practice. In case there is no system compatible reader at the extension tube end, manual tag reading (with possibly a button press on a pump menu) of its contents, i.e. a premixed reservoir, or drug+diluent tags reading and concentration calculation are done as described herein. The pump then adjusts the infusion protocol for each reservoir according to the prescription or the manual programming with readymade concentrations so as to avoid medication errors.

With such arrangement, the pump 10 has a periscope for its label reader camera 40, preferably comprising a rotating and/or unfolding articulated lever 42 at one of its sides with an inclined, preferably by 45 degrees, mirror 44 at its distant end. The lever 42 when in storage is folded along the pump body and when in use is rotated upwards extending higher than the pump 10 towards the tags 20, 28. Another embodiment may have no stylus or lever wherein the mirror 44 is close to the camera 40. The pump 10 has a barcode reader camera 40 on its top part that can read both tags 20, 28 at the lower part of the reservoir 2 with the mix 4 and the drug vial 26 through the inclined mirror 44. In another embodiment, the camera is held at the top end of a stem above the pump body, that may have an adjustable viewing angle so as to read even standard barcodes placed in the middle of the medication reservoir body so that different from the embodiment of FIG. 4 the tags 20 and 28 are shown in any part of the medication reservoir body. The mirror 44 diverts the view of the camera 40 by an angle, preferably by 90 degrees, to the tags 20, 28 so that the camera 40 reads them automatically and anytime as described above so as to assure that the correct drug is delivered to the correct patient. For doing so, a special software for the barcode label reader camera image processing is needed while usually RFID readers (that can also be used) can read more than one labels at once. This software may mask all other barcodes in the image and process one at a time.

In another preferred embodiment, in case of using an empty drug vial receptacle on reservoir, there is a receptacle 24 at the bottom of the reservoir 2 close to the placement of its own lower tag 20, where the nurse can place the empty vial 26 of the mix (FIGS. 1a and 2a), with its tag 28 being preferably a barcode print and facing at same side as the reservoir's tag 20 so that the camera 40 can read them both automatically as a variation of the embodiment of the FIG. 4. The said receptacle can be made as a flexible pocket from substantially the same material as the medication reservoir itself, bonded with its three lower edges to the medication reservoir, holding empty vial and showing through transparent pocket its tag towards the camera viewing window. The connecting dual spike with the elastic cap part 32 can be removed (FIG. 1c) or kept in place (FIGS. 2a and 2b). This is an alternative way for the same result as with the use of a peel-off barcode tag described herein. The drug name and mass (mg) is not written by hand prone to errors, and the automatic pump system calculation of the concentration prevents human errors as well as checking that the prescription and the contents of the reservoir 2 are identical. Since the weight and size of the vial 26 is small, this option not needing a pharmaceutical file modification is easy to implement. The holder or receptacle 24 for the vial 26 in a preferred embodiment may comprise a hollow plastic body 24a with a bottom 24c and an elastic opening 24b in front closing more than 180 degrees leaving an "Ω" type opening preferably about 150 degrees so that the vial 26 is press fitted therein and hold in place securely, while the tag 28 is visible in front. The nurse is instructed to place front visible the vial tag 28.

In the preferred embodiment there are two options: The drug vial receptacle and reservoir's label tags 20 and 28 are facing almost parallel or almost vertical to the ground. In a parallel way, the drug vial 26 is vertical to the ground (FIGS. 1 and 2) and its tag 28 is read by a periscope from the pump system or a camera on the back of the pump (not shown) that is high enough to directly read both tags, i.e. the one 28 of the vial 26 and the one 20 of the reservoir 2 (for doing so, the cartridge 12 can be placed lower on the pump 10 so that pump and its camera stays higher). In vertical orientation alternatively (not shown), the drug vial is hanged horizontally preferably by an "Ω" type of handle from above, with the barcode facing down and the reservoir barcode on a horizontal plate also facing down so that a camera facing upwards from the pump or pump system can read both tags and calculate concentration.

Therefore it is provided the reservoir 2 for a pharmaceutically produced diluent solution 4 and enables precautions for medication error prevention, wherein a tag 20 is placed on the medication reservoir 2, in particular at its edge portion 2a and/or near to an infusion tubing (not shown), the holder 24 is provided to support or hold a mix drug vial 26 for admixture with the content of the medication reservoir 2 and comprises an opening 24b in front so as to expose the tag 28 of the vial 26, wherein said tag 28 is placed close to the reservoir tag 20 so that both can be read by a tag reader without human intervention. The reservoir 2 may have as outlet port 6 a connecting tube for infusion by a pump 10 with a connector 8 that can hold the weight of the pump 10 when its infusion set is connected to the reservoir 2 and the pump to its infusion set.

In a manual mode, the nurse points the pump, preferably embodied as a miniature handy pump, towards the patient tag (without using a mirror, if provided), then towards the readymade premix drug and reads its standard pharmaceutical tag on its surface. In case of using a premixed drug, the pump reads from the drug library the concentration and infusion rate limits.

If the mix is done locally (as an admixture) and the nurse points the pump towards and reads first the drug label, it is understood that a diluent has to be scanned, too, so that when the nurse the pump points towards the reservoir, the pump reads the diluent label, gets from the drug library its volume, diluent type and concentration (for example 0.9% sodium chloride) and calculates the mix concentration with the drug previously scanned. The pump then calculates the limits for the infusion rate of the mix from the drug library information. This is a manual two step process instead of automatic reading of two tags as above described. Of course the reading can also be done from a flow sensor combined with a tag reader and possibly a drip chamber low level detector.

In this preferred embodiment the empty drug vial 26 can be kept in the holder 24 which may be alternatively embodied as a recess, a handle or a plastic bag and attached anywhere on the reservoir 2 just for documentation and error avoidance.

A pump system, that is small and lightweight enough with high battery autonomy can be used by a drug company as part of a drug-device combination, where infusion is sold as a service, wherein the drug company provides the drug and solution reservoir, the consumable and the miniature handy pump collects the pump for disinfection and reuses at the end of the infusion so as to assure maintenance and repair of a bank of pumps in a hospital.

In all preferred embodiments described above, all safety conditions as emphasized before are met:
a) The Infusion system scans two tags 20, 28 of drug and diluter together any time before the infusion starts or during the infusion wherein for doing so the two tags 20, 28 are arranged close to each other so to be read by one camera reading.
b) Evidence on diluter and drug data are kept during the entire infusion without the need of manual inscription.
c) A dilution concentration calculation is done by the infusion system so as to avoid manual errors.
d) It is checked whether or not the correct drug and concentration is delivered to the patient according to the prescription.

The drug vial receptacle or holder 24 may be used in both cases: Transportation from pharmacy to an admixture site when the vial 26 is full, as well as after having done the admixture, when the vial 26 is empty, during infusion or after it for documentation.

In another preferred embodiment, a distant pump may be part of an infusion set with a drip chamber and a female connector on top to be connected to the outlet port 6 provided as male connector, or the reservoir 2 comprises a standard tube for a spike connector which most drip chambers have, wherein an electronic device reads, like or as a flow sensor, the drips created in the drip chamber and also both tags 20, 28 together by means of a built-in camera. A preferable combination of a flow sensor and the tag reader can also make the infusion safe when using a distant pump. Furthermore, an electronic device can read the level of the fluid in the drip chamber and give an alarm in case of low level and a risk of air coming in the line. The electronic device is (by cable or wirelessly) connected to the said distant pump to make the infusion safe. So, said reservoir 2 for infusion described here can be used for both direct or distant pump reading and safe infusion.

The infusion pump user interface in the present invention is much easier to use and with less time consuming than prior art as most programming procedures are automatic and self-adaptable as shown below. Specifically, at start, the pump starts the tag reader and tries to find a tag to read, be it a patient, a nurse, a location or a drug diluent or diluter fluid tag. If it finds one, from libraries previously downloaded or by direct communication with the hospital server it understands what part of the process is already done and displays it. From the read tag itself by interpretation it understands what is missing. If for ex-ample a matching protocol gives a caregiver name to check, so that the user interface will ask a scan for the caregiver or whatever else is not already scanned but is present in the protocol. The nurse can scan as many as all of the above needed tags without interruption from the system which stores each one and at the end of the scanning presents all information read. The scan can also be done on demand by pressing a button. If a patient is not scanned, user interface can ask the user to scan the patient or manually enter its ID or name. The user interface also asks for a scan or enter by keyboard what else is missing for choosing a protocol and if a protocol is found then drugs to check.

If it is a patient tag, it downloads the latest protocols for the patient, the time to infuse if any and delivery route if any so that the nurse can check the 5R protocol. If it is only one medication tag, the user interface asks if it is the only one to scan, in case of premix drugs or just a saline infusion, if answer is no, then it asks to scan a secondary tag of a mix. Then the user interface asks if the read volumes need to be edited or not, or bypasses it by showing a next option. The editing of the protocol takes place, when the user interface shows all information found saying "check for compliance".

If the admixture matches a protocol from prescription electronic file or CERNER/EPIC drug delivery programmers, then if 5R data are present it asks the nurse to check the delivery route. If the time to infuse is present, the user interface asks if the delivery can be postponed till a time match, and the nurse can bypass this step. The protocol to be infused can be automatically found by several ways, if a patient is scanned or entered, drug name or time to infuse can find the correct protocol from a prescription list. So in case EPIC/CERNER communication is online, time of the day will download the correct protocol to be infused next minutes, if not, scanning drug diluent or premix drug reservoir will allow for the known patient correct protocol to be downloaded or chosen from a local database. So questions about therapy, body weight and surface area, age etc. can be omitted. After all that the user interface warns the nurse if the line is primed and if ok, it starts the infusion. After infusion the user interface sends infusion compliance data to the electronic medical record of the patient. In case of a piggyback infusion, the process of reading and checking is repeated for both infusion lines.

By means of this user interface, as described above, the automatic scanning of two medication labels or manual scanning of them sequentially with the patient too, is indifferent to the process, dramatically easing infusion programming and set-up; so that it has a safety meaning only to the health system. In the present invention, the user interface interaction with user is not always the same sequence of questions and answers or selections of program flow, but algorithmically adaptable to what patient has scanned. And user can scan if not automatically, tags in any order. After that user interface asks to manual input what necessary as new information is or editing of the information found. The flow and density of the information depends on how explicit protocol is found in the database. If full 5R is written, then user must check delivery route and pump will check delivery time. If caregiver name is needed, then nurse has to be scanned, if not all those steps are omitted. In case the user interface and/or the infusion pump understand a change in a tag read during the infusion or each time the infusion is stopped and restarted, the diluent and diluter tags are read again to see if the same drug mix is present, and the user interface asks the user to check the volume to be infused if it has changed or to resume the same already being infused. This is not a standard step procedure, but an adaptive one for processing the information read or downloaded, avoiding needless steps and going just to what is missing to complete a programming process. Of course, a standard programming with no tag reading procedure can be used if no tag is read.

The invention claimed is:

1. An infusion device comprising:
a medication reservoir having at least a first port adapted to be coupled to an inlet port of an infusion equipment;
a first tag support provided at a protrusion extending from said medication reservoir and adapted to support a first tag storing information about content of the medication reservoir and to be read by a tag reader;
a second tag support provided at said medication reservoir, the second tag support comprising a vessel holder that is connected to the protrusion and adapted to support a separate vessel having a second tag storing information about content of the separate vessel, which content is to be discharged into said medication reservoir so as to mix it with the content of said medication reservoir,
wherein the vessel holder includes a bottom plate at a lower end, and the vessel holder is open at an upper end facing a second port of the medication reservoir,
wherein said first tag support and said second tag support are provided to arrange and orientate both the first tag and the second tag so as to enable the tag reader to read said first tag and said second tag at a same time; and
a processing unit adapted to receive from a remote server data and to process said data in accordance with the information read by the tag reader from said first tag and said second tag,
wherein said processing unit is further adapted to calculate a concentration of the content contained in said medication reservoir and the content to be taken from the separate vessel by using the information obtained by the tag reader after having read said first tag and said second tag and to start with said calculation in accordance with a start of a reading operation of the tag reader.

2. The device according to claim 1, wherein said first tag support and said second tag support are provided to arrange and orientate both the first and second tags so as to enable the tag reader to read said first tag and said second tag, in a same perspective and/or in a same viewing window.

3. The device according to claim 1, wherein said second tag support is arranged adjacent and/or close to said first tag support.

4. The device according to claim 1, wherein said first tag support and/or said second tag support is provided adjacent and/or close to said first port of said medication reservoir.

5. The device according to claim 1, wherein said first tag support forms a first tag support portion or region provided at said medication reservoir and said second tag support forms a second tag support portion or region also provided at said medication reservoir, wherein said first tag support region or portion is provided to accommodate said first tag by attaching or printing it at said first tag support region or portion and/or said second tag support region or portion is provided to accommodate said second tag by self adhesively attaching it to said second tag support region or portion.

6. The device according to claim 1, wherein said first tag support and/or said second tag support is provided adjacent and/or close to a lower edge portion of said medication reservoir and/or hangs down from the lower edge portion of said medication reservoir.

7. The device according to claim 1, wherein said protrusion is additionally provided with said second tag support, wherein said protrusion comprises a second tag support portion which forms said second tag support.

8. The device according to claim 1, wherein said vessel holder is provided to hold the separate vessel in a vertical orientation with its opening facing upwards when the infusion device is in its operational mode.

9. The device according to claim 1, wherein said vessel holder is provided to hold the separate vessel in about a horizontal orientation with its opening facing sideways when the infusion device is in its operational mode, wherein said vessel holder is further provided to hold the separate vessel with its second tag facing downwards.

10. The device according to claim 1, wherein said second tag support is comprised of said vessel holder which is adapted to removably attach the separate vessel which comprises the second tag and is provided to hold the separate vessel so as to orientate its second tag to the tag reader.

11. The device according to claim 10, wherein said vessel holder comprises a hollow body adapted to accommodate the separate vessel and including a transparent window or an opening which is provided to enable the second tag of the separate vessel to be exposed and to be read by the tag reader.

12. The device according to claim 1, wherein said vessel holder is provided as a pocket which is at least partly transparent and/or made of a same material as the medication reservoir.

13. The device according to claim 1, wherein said vessel holder comprises a clamping mechanism for holding the separate vessel by clamping effect.

14. The device according to claim 11, wherein said hollow body has a tubular shape with a "Ω"-like cross section, said opening extends over an angular range less than 180 degrees, in a cross section plane and further extends along an entire length of the hollow body in an orientation transversely to said cross section plane, and said hollow body comprises elastic material at least in its portions bounding said opening.

15. The device according to claim 1, wherein the second port is adapted to be coupled to an opening of the separate vessel, wherein said second port comprises a connector which is a tap closing connector or an elastic self-closing connector.

16. The device according to claim 15, wherein said second port at said medication reservoir is arranged adjacent to the vessel holder, but in such a distance thereto that there is enough space which allows attachment of the separate vessel to said vessel holder and detachment of the separate vessel from said vessel holder.

17. The device according to claim 16, wherein said second port and the vessel holder are arranged relative to each other so that said second port faces to the opening of the separate vessel when attached to said vessel holder.

18. The device according to claim 1, further comprising the tag reader.

19. The device according to claim 18, wherein said tag reader is mounted to a support which is provided to adjust said tag reader so as to bring it in alignment to at least one of the tags so as to enable said tag reader to read said tag.

20. The device according to claim 19, wherein said support is provided to adjust a distance of said tag reader to said medication reservoir.

21. The device according to claim 18, wherein said tag reader comprises a camera adapted to read the tags.

22. The device according to claim 21, wherein said tag reader further comprises at least one mirror and an adjustment equipment adapted to adjust a viewing angle and/or a position, in particular a height, of said mirror relative to both said tags so as to enable the camera to read said tags, in a same perspective and/or in a same viewing window.

23. The device according to claim 1, further comprising the infusion equipment which includes the tag reader.

24. The device according to claim 23, wherein said infusion equipment includes a pump mechanism unit.

25. The device according to claim 23, wherein said infusion equipment includes an infusion pump comprising a first part which includes a pump mechanism and is provided with the inlet port, and a second part including said tag reader and a motor for driving the pump mechanism of the first part, wherein the first part is attachable to the second part for operation of the infusion pump.

26. The device according to claim 23, wherein said infusion equipment comprises a flow detector including said tag reader.

27. The device according to claim 1, wherein said first tag is provided to store and indicate characteristics of a diluter and said second tag is provided to store and indicate characteristics of a diluent.

28. The device according to claim 1, wherein said data received from the processing unit comprises drug library information, infusion protocol and infusion limits, and wherein the processing unit is adapted to process said data in accordance with the information read from said tags.

29. The device according to claim 28, wherein said processing unit is further adapted to calculate a concentration of a diluter contained in said medication reservoir and a diluent to be taken from the separate vessel by using the reading information obtained by the tag reader after having read the tags, wherein said processing unit is further adapted to start with said calculation in accordance with the start of a reading operation of the tag reader.

30. The device according to claim 29, wherein said processing unit comprises a user interface adapted to output questions asking how many vessels have been used for preparing an admixture.

31. The device according to claim 1, wherein said medication reservoir further comprises a third port adapted to be coupled to an output port of a further appliance.

32. The device according to claim 1, wherein said tag reader is further adapted to read a patient tag.

33. The device according to claim 1, wherein said second tag support is adapted to support a second tag which comprises a portion provided to be fixedly attached to a carrier substrate and to be cut through when the second tag is removed from the carrier substrate and attached to said second tag support.

34. The device according to claim 1, wherein the first tag is a barcode.

* * * * *